United States Patent [19]

Mahler et al.

[11] Patent Number: 5,665,266
[45] Date of Patent: Sep. 9, 1997

[54] AZEOTROPIC AND AZEOTROPE-LIKE COMPOSITIONS WITH HCL AND HALOCARBON

[75] Inventors: Barry Asher Mahler, Glen Mills; Vinci Martinez Felix, Kennett Square, both of Pa.; Ralph Newton Miller, Newark, Del.

[73] Assignee: E. I. Du Pont de Nemours and Company, Wilmington, Del.

[21] Appl. No.: 425,265

[22] Filed: Apr. 11, 1995

Related U.S. Application Data

[60] Division of Ser. No. 208,256, Mar. 9, 1994, abandoned, which is a continuation-in-part of Ser. No. 55,486, Apr. 30, 1993, Pat. No. 5,421,964.

[51] Int. Cl.$^6$ .................. C09K 5/04; C11D 7/30; C11D 7/50
[52] U.S. Cl. .................. 252/67; 510/412; 510/177
[58] Field of Search .................. 252/172, DIG. 9, 252/143, 67; 203/67; 510/412, 177

[56] References Cited

U.S. PATENT DOCUMENTS

| | | | |
|---|---|---|---|
| 1,892,652 | 12/1932 | Heath | 203/67 |
| 2,478,362 | 8/1949 | Benning | 202/51 |
| 3,347,021 | 10/1967 | Hutton | 55/71 |
| 3,505,233 | 4/1970 | Clark et al. | 252/67 |
| 3,617,209 | 11/1971 | Massonne et al. | 23/154 |
| 3,859,424 | 1/1975 | Scherer et al. | 423/472 |
| 4,154,804 | 5/1979 | Walker et al. | 423/240 |
| 4,643,851 | 2/1987 | Cheminal et al. | 260/544 Y |
| 4,678,859 | 7/1987 | Rudershausen | 570/163 |
| 5,049,241 | 9/1991 | Leverett et al. | 203/67 |
| 5,087,329 | 2/1992 | Felix | 203/67 |
| 5,211,817 | 5/1993 | Adams et al. | 203/82 |
| 5,345,017 | 9/1994 | Rao et al. | 570/227 |
| 5,346,595 | 9/1994 | Clemmer et al. | 203/75 |
| 5,523,498 | 6/1996 | Manzer et al. | 570/156 |

FOREIGN PATENT DOCUMENTS

| | | |
|---|---|---|
| 0503771 | 9/1992 | European Pat. Off. |
| 3-099026 | 4/1991 | Japan. |
| WO91/14667 | 10/1991 | WIPO. |
| WO93/2355 | 11/1993 | WIPO. |
| 94/13609 | 6/1994 | WIPO. |
| 94/16988 | 8/1994 | WIPO. |
| WO95/27689 | 10/1995 | WIPO. |

OTHER PUBLICATIONS

*Phase Equilibrium In Process Design*, Harold R. Null, pp. 124–126.
"Selecting the Agent for Distillation", Azeotropic & Extractive Distillation, L. Berg, pp. 52–57, vol. 65, No. 9, of *Chemical Engineering Progress* Sep. 1969.
*The Properties of Gases and Liquids*, 4th Edition, McGraw–Hill Publisher, Reid, Prausnitz & Poling, pp. 241–387.
Activity Coefficients, pp. 165–244.

*Primary Examiner*—Douglas J. McGinty

[57] ABSTRACT

The present invention discloses azeotropic or azeotrope-like compositions which include HCl that can be employed in a distillation or an extractive distillation process for separating HCl from pentafluoroethane, chloropentafluoroethane, chlorotrifluoroethane, trifluoromethane, and other fully saturated and unsaturated fluorocarbons, chlorofluorocarbons and chlorocarbons.

3 Claims, 6 Drawing Sheets

AZEOTROPIC AND AZEOTROPE-LIKE COMPOSITIONS WITH HCL AND HALOCARBON

CROSS-REFERENCE TO RELATED PATENT APPLICATION

This is a division of application Ser. No. 08/298,256 filed Mar. 9, 1994, now abandoned, which is a continuation-in-part of Ser. No. 08/055,486, filed Apr. 30, 1993, now U.S. Pat. No. 5,421,964, in the names of Barry A. Mahler et al., and entitled "Process For Separating HCl and Halocarbons"; the entire disclosure of which is hereby incorporated by reference.

FIELD OF THE INVENTION

The present invention relates to the field of separating HCl from a mixture comprising HCl and one or more halocarbons.

BACKGROUND OF THE INVENTION

Hydrofluorocarbons (HFCs), such as pentafluoroethane (HFC-125), are non-chlorine containing fluorocarbons that can be used as a refrigerant, blowing agent, propellant, fire extinguishing agent, sterilant carrier gas, among other valuable uses. By being non-chlorine containing, HFCs are believed to have less effects upon the earth's ozone layer.

One method for making pentafluoroethane comprises chlorofluorinating perchloroethylene to produce a mixture comprising trichlorotrifluoroethane (CFC-113), dichlorotetrafluoroethane (CFC-114), and dichlorotrifluoroethane (HCFC-123), along with by-product HCl. After removing at least some HCl and trichlorotrifluoroethane, the remaining mixture can be fluorinated by various processes thereby producing a mixture containing pentafluoroethane (HFC-125), chloropentafluoroethane (CFC-115), by-product HCl and lesser amounts of other fluorinated and chlorinated compounds, e.g., chlorotrifluoroethane (CFC-13) and trifluoromethane (HFC-23).

Certain halocarbons have been separated using conventional distillation. Another distillation method relates to extractive distillation. Procedures which have been used for predicting what extractive agents are likely to be effective in a given separation method have been described by L. Berg in an article published by Chem. Eng. Progress, Vol. 65, No. 9, pages 52–57, September 1969; the contents of which are hereby incorporated by reference. In discussing extractive distillation, it was stated in the previously identified article that ". . . hydrogen bonds appear to be an important factor since all successful extractive distillation agents are highly hydrogen bonded liquids. Thus, the criteria for successful extractive agents are that they boil considerably higher than the compounds being separated, form no minimum azeotropes with the components, and be a highly hydrogen bonded liquid, that is, Class I or Class II of the hydrogen bond classification. Phenols, aromatic amines (aniline and its derivatives), higher alcohols, glycols, etc. are examples of successful extractive agents."

SUMMARY OF THE INVENTION

The economic feasibility of a process for manufacturing certain halocarbons is dependent upon obtaining a useful HCl by-product. HCl is used in the pharmaceutical and food product industries. However, the utility of HCl in such industries typically requires that the residual halocarbon quantity be relatively low, e.g., typically less than about 100 ppm by weight of halocarbon in the HCl. Conventional distillation processes have been unable to obtain HCl product which is substantially free from halocarbons. By substantially free from halocarbons it is meant that the HCl product contains less than about 100 ppm by weight halocarbon. Normally, the substantially halocarbon free HCl product is anhydrous, e.g., containing less than about 100 ppm water.

The present invention solves the problems associated with conventional distillation processes, and relates to an extractive distillation process for separating HCl from one or more halocarbons such as pentafluoroethane, chloropentafluoroethane, chlorotrifluoromethane, trifluoromethane and other fully saturated and unsaturated fluorocarbons, and/or chlorocarbons, all optionally containing hydrogen. The extractive distillation process of the invention employs certain compounds or extractive agents that are not highly hydrogen bonded. By "not highly hydrogen bonded" it is meant that the extractive agents are not characterized as being Class I or Class II of the hydrogen bond classification.

The present invention provides a method of removing halocarbons from HCl wherein the halocarbons comprise at least one member selected from the group of saturated fluorocarbons, saturated and unsaturated hydrofluorocarbons, saturated and unsaturated hydrochlorofluorocarbons, saturated and unsaturated chlorofluorocarbons, saturated and unsaturated hydrochlorocarbons, saturated and unsaturated chlorocarbons, among others.

One aspect of the present invention relates to a process for separating HCl from a first mixture of HCl and at least one member from the group of pentafluoroethane, chloropentafluoroethane, chlorotrifluoromethane, trifluoromethane, among others. The process comprises the steps of:

adding a fluorocarbon, chlorofluorocarbons or chlorocarbon extractive agent having 1 to 5 carbon atoms, either saturated or unsaturated, optionally including hydrogen; and having a boiling point at atmospheric pressure typically greater than about −48° C., normally greater than about −15° C., and less than about 120° C., usually less than about 80° C., to the first mixture in order to form a second mixture, separating HCl from the halocarbons in the second mixture by extractively distilling the second mixture in an extractive distillation zone, and recovering HCl as an overhead product which is substantially free from the halocarbons of the first mixture.

In addition to being not highly hydrogen bonded, the extractive agent used in the present invention can be related chemically to the halocarbon which is being separated from the HCl. By "chemically related" it is meant that the extractive agent comprises a halocarbon optionally containing hydrogen. Examples of such related extractive agents comprise one or more compounds having 1–5 carbons atoms and which include hydrogen and/or fluorine and/or chlorine atoms. Using a chemically related extracting agent typically minimizes the risk of introducing extraneous impurities into the halocarbons being separated.

Representative extractive agents suitable for use in the present invention comprise one or more saturated or unsaturated C1 through C5 compounds such as fluorocarbons, chlorofluorocarbons, or chlorocarbons, each optionally containing hydrogen, among others. Specific examples of suitable extractive agents comprise or consist essentially of at least one member selected from the group of 2-chloro-1,1,1,2-tetrafluoroethane (HCFC-124), 2,2-dichloro-1,1,1-trifluoroethane (HCFC-123), 2,2-dichloro-1,1,1,2-tetrafluoroethane (CFC-114a), 1,1,1,2,2-pentafluoroethane (HFC-125), 1-chloro-1,1,2,2,2-pentafluoroethane (CFC-115), their isomers, mixtures thereof, among others.

Another aspect of the invention relates to azeotropic and azeotrope-like compositions that can form between a mixture consisting essentially of at least two members from the group of HCl, CFC-13, HFC-23, CFC-115, HFC-125, among others.

A further aspect of the invention relates to using the azeotropic and azeotrope-like compositions for separating the components of the first mixture.

DETAILED DESCRIPTION

Figure 1:
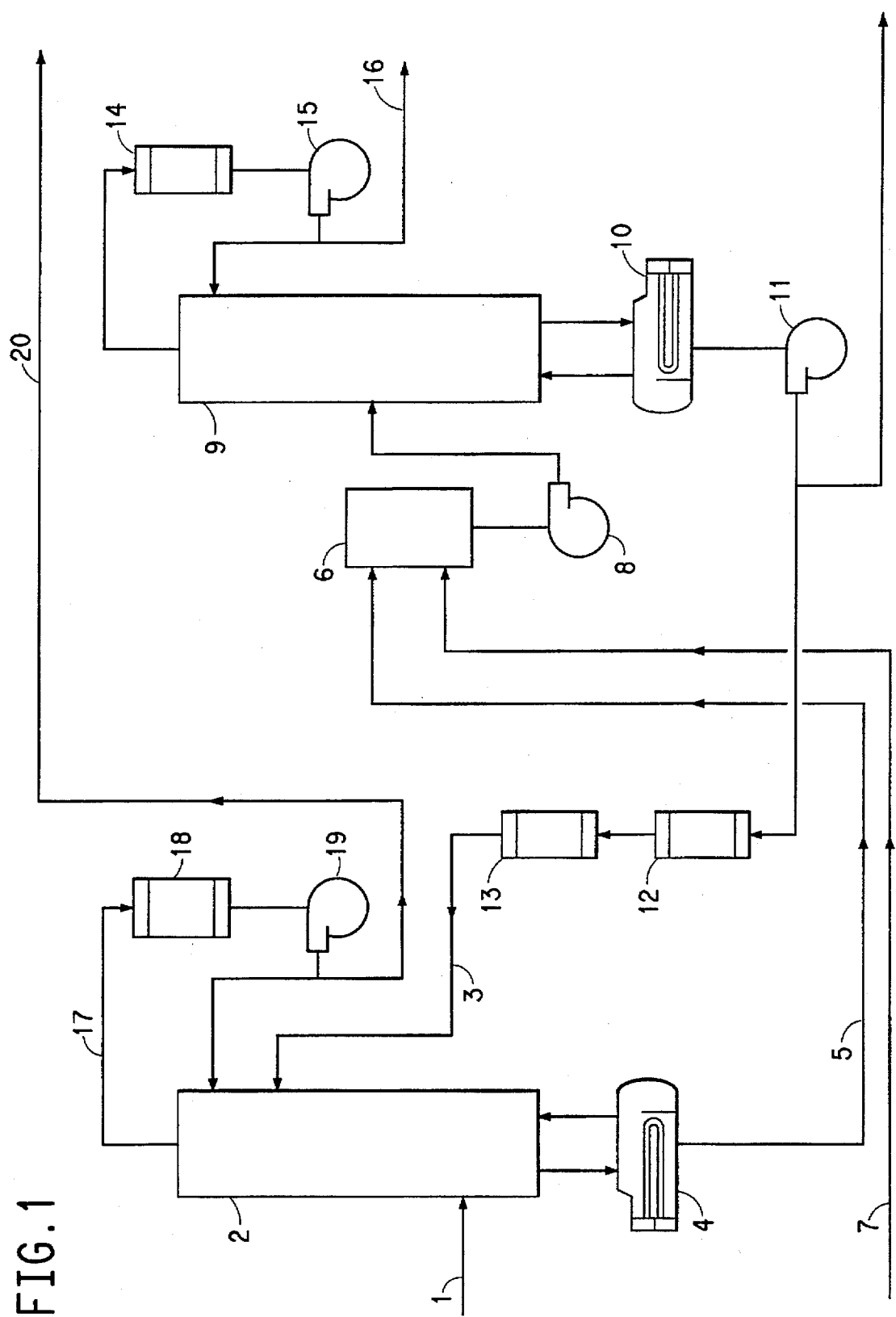
FIG. 1—FIG. 1 is a schematic diagram of an extractive distillation system which can be used for practicing the process of the invention.

HCl and pentafluoroethane (HFC-125) in their separated and generally pure states have atmospheric pressure boiling points of about −85° C. and about −49° C., respectively. However, a mixture comprising HCl and HFC-125 exhibits non-ideal vapor-liquid behavior such that the relative volatility of HCl to pentafluoroethane becomes extremely low when approaching 100% HCl purity, e.g., the relative volatility approaches 1.0. As a result, conventional distillation processes are incapable of efficiently separating pure HCl from this mixture.

To determine the relative volatility of HCl and a halocarbon, e.g., pentafluoroethane (HFC-125), the so-called PTx Method was used. In the PTx method, the total absolute pressure in a cell of known volume is measured at a constant temperature for various known binary compositions. Use of the PTx Method is described in greater detail in "Phase Equilibrium in Process Design", Wiley-Interscience Publisher, 1970, written by Harold R. Null, on Pages 124 through 126; the entire disclosure of which is hereby incorporated by reference.

These measurements can be reduced to equilibrium vapor and liquid compositions in the cell by an activity coefficient equation model, such as the Non-Random, Two-Liquid (NRTL) equation, to represent liquid phase non-idealities. Use of an activity coefficient equation, such as the NRTL equation, is described in greater detail in "The Properties of Gases and Liquids, 4th edition, McGraw-Hill—publisher, Reid, Prausnitz, and Poling—Authors, pages 241 through 387; and in "Phase Equilibria in Chemical Engineering", Butterworth Publishers, 1985, Stanley M. Walas—Author, pages 165 through 244; the entire disclosure of each of the previously identified references are hereby incorporated by reference.

Without wishing to be bound by any theory or explanation, it is believed that the NRTL equation can sufficiently predict whether or not HCl and HFC-125 mixtures and/or the following other HCl and halocarbon mixtures behave in an ideal manner, and can sufficiently predict the relative volatilities of the components in such mixtures.

The results of the PTx measurements for the HCl and HFC-125 mixture at −10° C. and the above series of calculations can be summarized generally in Table I below. Similar measurements were obtained and similar calculations were performed for other binary combinations of compounds which are related to the invention.

TABLE I

Vapor-Liquid Measurements on the HCl/HFC-125 System at −10° C.

| Mol % of HFC-125 in | | Pressure | Relative Volatility |
|---|---|---|---|
| Liquid | Vapor | psia | HCl/HFC-125 |
| 98.43 | 91.29 | 77.8 | 5.980 |
| 85.27 | 53.22 | 128.9 | 5.089 |
| 73.98 | 39.20 | 163.2 | 4.409 |
| 50.87 | 24.41 | 219.5 | 3.207 |
| 29.88 | 15.75 | 256.5 | 2.280 |
| 19.27 | 11.38 | 271.5 | 1.858 |
| 12.27 | 8.06 | 279.6 | 1.596 |
| 0.00 | 0.00 | 288.0 | 1.172 |

The relative volatility of HCl in comparison to pentafluoroethane at relatively low concentrations of HCl is sufficient to permit separating HCl by using conventional distillation methods, e.g., the relative volatility at low HCl concentrations is much greater than 1.0. However, the relative volatility approaches about 1.17 at high concentrations of HCl, e.g., when pentafluoroethane concentrations are near zero %. A relative volatility approaching 1.0 would render removal of low concentrations of HFC-125 from HCl by conventional distillation methods a costly operation requiring large and expensive distillation columns.

Even more difficult problems occur when separating relatively small quantities of chloropentafluoroethane (CFC-115), which has a boiling point at atmospheric pressure of about −39° C., from an HCl containing mixture. The results of PTx measurements and calculations for the HCl-chloropentafluoroethane system at −30° C. can be summarized generally in Table II below (and shown graphically in FIG. 2 which is discussed below in greater detail).

TABLE II

Vapor-Liquid Measurements on the HCl/CFC-115 System at −30° C.

| Mol % of CFC-115 in | | Pressure | Relative Volatility |
|---|---|---|---|
| Liquid | Vapor | psia | HCl/CFC-115 |
| 95.52 | 51.90 | 42.2 | 19.90 |
| 80.80 | 23.34 | 90.0 | 13.82 |
| 60.47 | 15.27 | 126.2 | 8.49 |
| 40.64 | 12.02 | 144.1 | 5.01 |
| 25.43 | 10.10 | 152.7 | 3.04 |
| 10.00 | 6.97 | 157.7 | 1.48 |

TABLE II-continued

Vapor-Liquid Measurements on the HCl/CFC-115 System at −30° C.

| Mol % of CFC-115 in | | Pressure | Relative Volatility |
|---|---|---|---|
| Liquid | Vapor | psia | HCl/CFC-115 |
| 6.99 | 5.76 | 158.5 | 1.23 |
| 5.03 | 4.70 | 158.8 | 1.05 |
| 3.97 | 4.00 | 158.9 | 0.95 |
| 1.96 | 2.31 | 158.6 | 0.85 |

The relative volatility of HCl in comparison to chloropentafluoroethane at relatively low concentrations of HCl is sufficient to permit separating HCl by using conventional distillation methods, e.g., the relative volatility at low HCl concentrations is much greater than 1.0. However, the relative volatility drops to 1.0 at chloropentafluoroethane concentrations near about 4 mole %, thereby indicating the formation of an azeotropic or azeotrope-like composition. The formation of an azeotropic or azeotrope-like composition is also indicated by mixtures of HCl and chloropentafluoroethane which at a given temperature have a higher vapor pressure than other mixtures as well as a higher vapor pressure than either pure component at that temperature, e.g., refer to FIG. 2. Such azeotropic or azeotrope-like formation would make it virtually impossible for conventional methods to produce HCl substantially free of chloropentafluoroethane from an HCl mixture containing more than about 4 mole % chloropentafluoroethane. While conventional distillation methods may be capable of separating mixtures, which contain less than about 4 mole % chloropentafluoroethane, into the azeotropic composition and pure HCl, a significant amount of the HCl would still remain as the azeotropic or near azeotropic mixture in proportion to the concentration of chloropentafluoroethane present in the starting mixture. In addition, the relative volatility for such mixtures is sufficiently dose to 1.0 that an impractically large distillation column would be required for separation.

Whenever used in the specification and appended claims the terms below are intended to have the following definitions.

By "azeotrope" or "azeotropic" composition is meant a constant boiling liquid admixture of two or more substances that behaves as a single substance. One way to characterize an azeotropic composition or mixture is that the vapor produced by partial evaporation or distillation of the liquid has the same composition as the liquid from which it was evaporated or distilled, e.g., the admixture distills/refluxes without compositional change. Constant boiling compositions are characterized as azeotropic because they exhibit either a maximum or minimum boiling point, as compared with that of the non-azeotropic mixtures of the same components. An azeotropic composition can also be characterized as the maximum or minimum vapor pressure for a mixture at a given temperature when plotted as a function of mole fraction.

By "azeotrope-like" composition is meant a constant boiling, or substantially constant boiling, liquid admixture of two or more substances that behaves as a single substance. One way to characterize an azeotrope-like composition is that the vapor produced by partial evaporation or distillation of the liquid has substantially the same composition as the liquid from which it was evaporated or distilled, e.g., the admixture distills/refluxes without substantial compositional change. An azeotrope-like composition can also be characterized by the area, which is shown by plotting vapor pressure at given temperature as a function of mole fraction, that is adjacent to the maximum or minimum vapor pressure.

Typically, a composition is azeotrope-like, if, after about 50 weight percent of the composition is removed such as by evaporation or boiling off, the change between the original composition and the composition remaining is less than about 6% and normally less than about 3% relative to the original composition.

By "effective amount" is intended to refer to the amount of each component of the inventive compositions which, when combined, results in the formation of an azeotropic or azeotrope-like composition. This definition includes the amounts of each component, which amounts may vary depending on the pressure applied to the composition so long as the azeotropic or azeotrope-like compositions continue to exist at the different pressures, but with possible different boiling points. Effective amount also includes the mounts, such as may be expressed in weight percentages, of each component of the compositions of the instant invention which form azeotropic or azeotrope-like compositions at temperatures or pressures other than as described herein. Therefore, included in this invention are azeotropic or azeotrope-like compositions consisting essentially of effective mounts of at least one of HCl or HFC-125 and at least one fluorinated molecule such that after about 50 weight percent of an original composition is evaporated or boiled off to produce a remaining composition, the change between the original composition and the remaining composition is typically no more than about 6% and normally no more than about 3% or less relative to the original composition.

It is possible to characterize, in effect, a constant boiling admixture which may appear under many guises, depending upon the conditions chosen, by any of several criteria:

The composition can be defined as an azeotrope of HCl ("A") and a halocarbon ("B"), or of HFC-125 ("C") and CFC-115 ("D"), among others, because the term "azeotrope" is at once both definitive and limitative, and requires effective amounts of A,B (or C, D) for this unique composition of matter which can be a constant boiling composition.

It is well known by those skilled in the art, that, at different pressures, the composition of a given azeotrope will vary at least to some degree, and changes in pressure will also change, at least to some degree, the boiling point temperature. Thus, an azeotrope of HCl ("A") and a halo carbon ("B") or of HFC-125 ("C") and CFC-115 ("D"), among others, represents a unique type of relationship but with a variable composition which depends on temperature and/or pressure. Therefore, compositional ranges, rather than fixed compositions, are often used to define azeotropes.

The composition can be defined as a particular weight percent relationship or mole percent relationship of HCl ("A") and a fluorocarbon ("B") or of HFC-125 ("C") and CFC-115 ("D"), among others, while recognizing that such specific values point out only one particular relationship and that in actuality, a series of such relationships, represented by A,B (or C, D) actually exist for a given azeotrope, varied by the influence of pressure.

An azeotrope of HCl ("A") and a halocarbon ("B") or of HFC-125 ("C") and CFC-115 ("D"), among others, can be characterized by defining the compositions as an azeotrope characterized by a boiling point at a given pressure, thus giving identifying characteristics without unduly limiting the scope of the invention by a specific numerical composition, which is limited by and is only as accurate as the analytical equipment available.

The azeotrope or azeotrope-like compositions of the present invention may be formed by operating a conventional distillation apparatus, when practicing the inventive extractive distillation method, and by combining effective amounts of the components by any convenient method including mixing, combining, among others. For best results, a preferred method is to weigh the desired component amounts, and thereafter combine them in an appropriate container.

HCl and chlorotrifluoromethane (CFC-13) may form an azeotropic composition consisting essentially of about 37 mole % chlorotrifluoroethane and about 63 mole % HCl with a pressure of about 277 psia when at a temperature of about −20° C., e.g., refer to FIG. 3 which is discussed below in greater detail. Conventional distillation methods would be expected to produce a separated mixture wherein a significant portion of the HCl remains in the azeotropic or azeotrope-like mixture. In addition, the relative volatility for such mixtures is sufficiently close to 1.0 that an impractically large distillation column would be required for separation.

HCl and trifluoromethane (HFC-23) may also form an azeotropic composition consisting essentially of about 45 mole % trifluoromethane and about 55 mole % HCl with a pressure of about 262 psia when at a temperature of about −20° C., e.g., refer to FIG. 4 which is discussed below in greater detail. Conventional distillation methods would be expected to produce a separated mixture wherein a significant portion of the HCl remains in the azeotropic or azeotropic-like mixture. In addition, the relative volatility for such mixtures is sufficiently close to 1.0 that an impractically large distillation column would be required for separation.

The problems associated with conventional distillation methods are overcome in the present invention by using an extractive distillation method. Extractive distillation depends upon the ability of certain extractive agents to increase the relative volatility of the compounds to be separated. Extractive distillation is typically performed by operating a continuous distillation column, which comprises a multi-stage distillation column, with a minimum of two feed points, e.g., introducing the extractive agent at a first feed point which is located above the second feed point that is used for introducing the mixture to be separated, a reboiler and an overhead condenser for returning reflux to the column.

Given the relative volatilities of HFC-125, CFC-115, CFC-13, HFC-23 and HCl, it was a surprising and an unexpected result that using an extractive distillation process can purify or separate HCl. It was a particularly surprising and an unexpected result that the inventive process is capable of separating HCl from mixtures containing HFC-125 and HCl, CFC-115 and HCl, CFC-13 and HCl, or HFC-23 and HCl; wherein at least 99.0% of the HCl is recovered and the recovered HCl has at least about 99.99% by weight purity.

In one aspect of the invention, an extractive agent, e.g., 2-chloro-1,1,1,2-tetrafluoroethane (HCFC-124), is introduced at an upper feed point of the distillation column, whereas the mixture requiring separation, e.g. HCl and pentafluoroethane, is introduced at a relatively lower feed point of the column. The liquid extractive agent passes downwardly through trays which are located in the center of the column. While in the presence of the extractive agent, HCl is relatively more volatile than the halocarbon, thereby allowing HCl, which is substantially free from the halocarbon, to escape from the top of the column. The liberated HCl is condensed using known techniques, e.g., the HCl is condensed using conventional reflux condensers. At least a portion of this condensed HCl stream can be returned to the top of the column as reflux, and the remainder recovered as a useful product. The ratio of the condensed material, which is returned to the column, to the material removed as product is commonly referred to as the reflux ratio. The halocarbon and extractive agent exiting the column can then be passed to a stripper or distillation column for separation by using conventional distillation or other known methods and, if desired, recycle of the extractive agent to the extractive distillation column.

The specific conditions which can be used for practicing the invention depend upon a number of parameters such as the diameter of the distillation column, feed points, number of separation stages in the column, among others. The operating pressure of the distillation system may range from about 15 to 350 psia, normally about 50 to 300 psia. Typically, an increase in the extractant feed rate relative to the crude HCl feed rate causes an increase in the purity of the separated HCl. Normally, increasing the reflux ratio results in an increased HCl product purity; but generally the reflux ratio ranges between 1/1 to 10/1, normally 2/1 to 3/1. The temperature of the condenser, which is located adjacent to the top of the column, is normally sufficient to substantially fully condense the HCl and optional trace quantities of halocarbon that are exiting from the top of the extractive distillation column, or is that temperature required to achieve the desired reflux ratio by partial condensation.

While the above description places particular emphasis on using extractive distillation agents, certain aspects of the invention relate to azeotropic or azeotrope-like compositions. The formation of an azeotropic or near azeotrope mixture between HFC-125 and CFC-115 was indicated by the vapor-liquid equilibrium (VLE) pinch point that was disclosed in commonly assigned U.S. Pat. No. 5,087,329; the entire disclosure of which is hereby incorporated by reference. Although best results are obtained herein by using process parameters that minimize formation of azeotropic or azeotrope-like mixtures, such mixtures can be used to purify an admixture comprising HCl and one or more halocarbons. For example, a conventional distillation column could be operated at conditions that cause formation of an azeotropic or azeotrope-like mixture that is withdrawn as an overhead product. The withdrawn azeotrope mixture can be condensed by using conventional means and, if desired, the components can be separated by using the inventive process described herein. The non-azeotropic components would be removed as bottoms from the column.

PTx measurements for the HFC-125 and CFC-115 system were obtained at 10° C. and NRTL parameters were calculated. The vapor pressure of the PTx cell is plotted in FIG. 5 as a function of composition. Using these parameters, calculations indicated the presence of a HFC-125 and CFC-115 azeotrope at relatively low temperatures. The results of these calculations at −50° C. are shown in FIG. 6, which indicates an azeotropic composition of about 88 mole % HFC-125 and 12 mole % CFC-115 having a pressure of about 13.5 psia. Without wishing to be bound by any theory or explanation, it is believed that by using a relatively low temperature, an azeotropic or azeotrope-like mixture can be formed between HFC-125 and CFC-115, e.g., an azeotropic mixture consisting essentially of about 90 to 95 mole % HFC-125 and 5 to 10 mole % CFC-115 when at a temperature of about −40° to −60° C. and a pressure of about 10 to 15 psia. The formation of such a mixture may permit distilling an HFC-125 and CFC-115 mixture, and removing CFC-115 as an HFC-125/CFC-115 azeotrope. By removing CFC-115 as an azeotropic or azeotrope-like mixture, a very high purity HFC-125 may be produced, e.g., HFC-125 having less than 100 ppm by weight residual CFC-115.

In some cases, a mixture of CFC-115 and HCl may exhibit azeotropic or azeotrope-like behavior, e.g., temperature/pressure/composition regions at which a vapor-liquid equilibrium (VLE) pinch occurs. For example, a mixture consisting essentially of about 96 mole % HCl and about 4 mole % CFC-115 is azeotropic at a temperature of about −30° C. and a pressure of about 159 psia.

An azeotropic or azeotrope-like mixture may be formed between a mixture consisting essentially of about 0.1 to about 5.0 mole % CFC-115 and about 95 to about 99.9 mole % HCl when at a temperature of about 25° to −50° C. and a pressure of about 75 to about 700 psia. Such a mixture may have a higher vapor pressure than either pure HCl or pure CFC-115. The formation of this azeotropic or azeotrope-like mixture may permit distilling a CFC-115 and HCl mixture, and removing CFC-115 as an CFC-115/HCl azeotrope. By removing CFC-115 as an azeotropic or azeotrope-like mixture, a very high purity HCl may be produced, e.g., 99.99% by weight pure HCl.

Further, an azeotropic or azeotrope-like composition may be formed between a mixture consisting essentially of about 33 to about 37 mole % CFC-13 and about 63, e.g., about 62, to about 67 mole % HCl when at a temperature of about 0° to −50° C. and a pressure of about 90 to about 500 psia. Such a mixture may have a higher vapor pressure than either pure HCl or pure CFC-13. The formation of such an azeotropic or azeotrope-like mixture may permit distilling a CFC-13 and HCl mixture, and removing CFC-13 as an CFC-13/HCl azeotrope. By removing CFC-13 as an azeotropic or azeotrope-like mixture, a very high purity HCl may be produced, e.g., 99.99% by weight pure HCl.

Another azeotropic or azeotrope-like composition may be formed between a mixture consisting essentially of about 43 to about 47 mole % HFC-23 and about 53 to about 57 mole % HCl when at a temperature of about 0° to −50° C. and a pressure of about 90 to about 500 psia. Such a mixture has a higher vapor pressure than either pure HCl or pure HFC-23. The formation of such an azeotrope may permit distilling a HFC-23 and HCl mixture, and removing HFC-23 as an HFC-23/HCl azeotropic or azeotrope-like mixture. By removing HFC-23 as an azeotropic or azeotrope-like mixture, a very high purity HCl may be produced, e.g., 99.99% by weight pure HCl.

In addition, the invention may be effective at removing other impurities from HCl. For example, impurities that have a relatively low boiling point, e.g., a boiling point at atmospheric pressure greater than about −100° C., can be removed from the HCl.

Referring now to the Figure, FIG. 1 schematically illustrates a system which can be used for operating the inventive extractive distillation process. A first mixture containing HCl and at least one halocarbon is supplied via conduit 1 to extraction column 2. At least one liquid extractive agent is supplied via conduit 3 to the extraction column 2, and introduced into column 3 at a location above the mixture 1. A second mixture comprising extractive agent, halocarbons from the first mixture, and trace amounts of HCl is removed from the column 3, and transported to steam heated reboiler 4. In some cases, the reboiler 4 is attached to the extractive column 2. The second mixture is supplied via conduit 5 to a feed tank 6. Supplemental liquid extractive agent is also supplied to feed tank 6 via conduit 7 thereby forming a third mixture or extraction agent recycle. A pump 8 transports the third mixture to a stripping column 9. Stripping column 9 separates the extractive agent from non-extractive agents. Extractive agent is removed from column 9 and supplied to a second steam heated reboiler 10. In some cases, the reboiler 10 is attached to column 9. Pump 11 transports the extractive agent from the reboiler 10 through a cold water chiller 12, and then to chiller 13. If necessary, excess quantities of extraction agent can be purged prior to reaching chiller 12. Typically, chiller 13 is operated at a temperature of about −25° C. After exiting chiller 13, the extraction agent is supplied via conduit 3 into extraction column 2.

The non-extractive agents or halocarbons exit from the top of stripping column 9 as an off gas, and are introduced into condenser 14, which is typically operated at a temperature of about −25° C. While under reflux conditions, pump 15 returns a portion of the halocarbon to the stripping column 9. The remaining portion of the halocarbon exits the system via conduit 16.

An off gas is also removed from extraction column 2, with the exception that the off gas from column 2 contains anhydrous HCl product which is substantially free from halocarbons of the first mixture. The HCl product is transported via conduit 17 to condenser 18. Condenser 18 is typically operated at a temperature of about −25° C. While under reflux conditions, pump 19 returns a portion of the HCl product to extraction column 2. The substantially anhydrous HCl products exits the system via conduit 20.

When an azeotrope is used for separating the first mixture, the column 2 is operated at conditions that cause formation of the desired azeotropic or azeotrope-like composition. The composition is condensed by using condenser 18. The non-azeotrope components of the first mixture exit column 2 via conduit 5.

The following Examples are provided to illustrate certain aspects of the present invention. Parts per million (ppm) concentrations are by weight unless otherwise specified. The following Examples employ the NRTL interaction parameters identified above. In all of the following Examples, the distillation column has 52 stages, and is operated at a pressure of about 265 psia. All Examples are based on an HCl feed stream containing about 5000 lb/hr of HCl. The HCl stream to be purified is introduced onto distillation column stage 40, and the extractant, if used, is fed onto column stage 5. The condenser is designated as stage 1. In each Example, the column distillate rate is adjusted to achieve a quantity of about 5 lb/hr of HCl in the column tails stream, i.e., the liquid exiting the bottom of the column. The Tables illustrate the resulting purity of the HCl stream for a particular reflux ratio. The extractive agent, its feed rate, and the composition of the HCl feed stream to be purified can also be varied for tailoring the process to accommodate the purity of product HCl desired.

EXAMPLE 1A

In this comparative example, no extractive distillation agent is used. A first feed stream of impure HCl (Mixture #1) contains 5,000 lb/hr of HCl, 10,000 lb/hr of HF, 5,000 lb/hr of HCFC-123, 5,000 lb/hr of HCFC-124 and 5,000 lb/hr of HFC-125. The amount of HFC-125 in the distilled HCl stream in parts per million (ppm) opposite the reflux ratio is tabulated generally in Table III below.

TABLE III

Separation of HFC-125 from HCl Mixture #1 using no Extractant

| Reflux Ratio | Lb/Hr HCl in Distillate | Lb/Hr HFC-125 in Distilled HCl | ppm (wt) of HFC-125 in HCl |
| --- | --- | --- | --- |
| 2/1 | 4,995 | 434 | 79,941 |
| 3/1 | 4,995 | 275 | 52,182 |
| 5/1 | 4,995 | 150 | 29,155 |
| 10/1 | 4,995 | 67 | 13,236 |
| 20/1 | 4,995 | 34 | 6,761 |
| 40/1 | 4,995 | 21 | 4,187 |

The reflux ratio is a key process parameter in that this ratio affects the gas and liquid flow rates within the column, which determine the required cross-sectional area and the energy requirements of the distillation column, which in turn determine or affect the overall capital cost, maintenance costs, and the operating cost for the purification step.

In this Example, the HCl distilled overhead contains over 4000 ppm of HFC-125 even when operating the conventional distillation column at relatively high reflux ratios.

EXAMPLE 1B

In this example, 15,000 lb/hr of HCFC-123 is used as the extractive distillation agent. The feed stream of impure HCl has substantially the same composition as in the previous example (Mixture #1). The amount of HFC-125 in the distilled HCl stream in parts per million (ppm) opposite the reflux ratio is tabulated generally in Table IV below:

TABLE IV

Separation of HFC-125 from HCl Mixture #1 using 15,000 lb/hr HCFC-123 as Extractant

| Reflux Ratio | Extractant Rate, Lb/Hr | Lb/Hr HFC-125, in Distilled HCl | ppm (wt) of HFC-125 in HCl |
| --- | --- | --- | --- |
| 1.5/1 | 15,000 | 96 | 18,857 |
| 2/1 | 15,000 | 36 | 7,156 |
| 3/1 | 15,000 | 15 | 2,994 |
| 5/1 | 15,000 | 9 | 1,799 |
| 10/1 | 15,000 | 8 | 1,599 |

The HFC-125 in the overhead HCl stream is reduced to about 1600 ppm by extractive distillation with HCFC-123 with a reflux ratio of 10. Compared to conventional distillation (Example 1A) at the same reflux ratio, the level of HFC-125 in the above distilled HCl is reduced from about 13,236 ppm to about 1600 ppm, or reduced by a factor of 8.

EXAMPLE 1C

In this example, the amount of the extractive agent, HCFC-123, is increased to about 25,000 lb/hr. The feed stream of impure HCl has the substantially same composition as Examples 1A and 1B. The amount of HFC-125 in the distilled HCl stream vs the reflux ratio is tabulated generally in Table V below:

TABLE V

Separation of HFC-125 from HCl Mixture #1 using 25,000 lb/hr HCFC-123 as extractant

| Reflux Ratio | Extractant Rate, Lb/Hr | Lb/Hr HFC-125, in Distilled HCl | ppm (wt) of HFC-125 in HCl |
| --- | --- | --- | --- |
| 2/1 | 25,000 | 7 | 1,399 |
| 3/1 | 25,000 | 2 | 400 |
| 5/1 | 25,000 | 1 | 200 |

The increased feed rate of extractive agent improves the purity of the distilled HCl in comparison to the previous example.

Compared to conventional distillation (Example 1A) at a comparable reflux ratio of 3.0, the level of HFC-125 in the distilled HCl is reduced from 52,182 ppm to 400 ppm, or reduced by a factor of 130. Table V illustrates that obtaining the same purity level of HCl as in Example 1C by conventional distillation would be completely impractical because of the required column size.

EXAMPLE 2A

In this comparative example, the feed stream of impure HCl (HCl Mixture #2) contains about 5,000 lb/hr of HCl, 5,000 lb/hr of HCFC-123 and 5,000 lb/hr of HFC-125. The amount of HFC-125 in the overhead purified HCl stream vs the reflux ratio is tabulated generally in Table VI below:

TABLE VI

Separation of HFC-125 from HCl Mixture #2 using no Extractant

| Reflux Ratio | Lb/Hr HCl in Distillate | Lb/Hr HFC-125, in Distilled HCl | ppm (wt) of HFC-125 in HCl |
| --- | --- | --- | --- |
| 2/1 | 4,995 | 429 | 79,093 |
| 3/1 | 4,995 | 272 | 51,642 |
| 5/1 | 4,995 | 149 | 28,966 |
| 10/1 | 4,995 | 66 | 13,041 |
| 20/1 | 4,995 | 33 | 6,563 |
| 40/1 | 4,995 | 20 | 3,988 |

Notwithstanding the relatively high reflux ratios, conventional distillation (Example 2A) is unable to produce HCl with low impurity levels from Mixture #2.

EXAMPLE 2B

In this example, about 15,000 lb/hr of HCFC-123 is used as the extractive distillation agent. The feed stream of impure HCl corresponds substantially to Mixture #2. The amount of HFC-125 in the overhead purified HCl stream vs the reflux ratio is tabulated generally in Table VII below:

TABLE VII

Separation of HFC-125 from HCl Mixture #2 using 15,000 lb/hr HCFC-123

| Reflux Ratio | Extractant Rate, Lb/Hr | Lb/Hr HFC-125, in Distilled HCl | ppm (wt) of HFC-125 in HCl |
| --- | --- | --- | --- |
| 1.5/1 | 15,000 | 71 | 14,015 |
| 2/1 | 15,000 | 31 | 6,168 |
| 3/1 | 15,000 | 14 | 2,795 |
| 5/1 | 15,000 | 8 | 1,599 |

Table VII illustrates that using HCFC-123 as an extractive agent produces a purified stream of HCl wherein the level of impurities is much lower than can be obtained by conventional distillation (Example 2A).

Compared to conventional distillation (Example 2A) at a comparable reflux ratio of 5.0, the level of HFC-125 in the distilled HCl is reduced from 28,966 ppm to 1599 ppm, or reduced by a factor of 18. Obtaining the same purity level of HCl as in Example 2B by conventional distillation would be completely impractical because of the size of column required.

EXAMPLE 2C

In this example, about 15,000 lb/hr of HCFC-124 is used as the extractive distillation agent in place of HCFC-123. The feed stream of impure HCl is substantially the same as in Examples 2A and 2B (Mixture #2). The amount of HFC-125 in the overhead purified HCl stream vs the reflux ratio is tabulated generally in Table VIII below:

TABLE VIII

Separation of HFC-125 from HCl Mixture #2 using 15,000 lb/hr HCFC-124

| Reflux Ratio | Extractant Rate, Lb/Hr | Lb/Hr HFC-125, in Distilled HCl | ppm (wt) of HFC-125 in HCl |
|---|---|---|---|
| 1.5/1 | 15,000 | 2.3 | 460 |
| 2/1 | 15,000 | 0.5 | 100 |
| 3/1 | 15,000 | 0.2 | 40 |

Results illustrated in Table VIII are substantially improved over Example 2B because HCFC-124 is a relatively more efficient extractive agent than HCFC-123.

Compared to conventional distillation (Example 2A) at a comparable reflux ratio of 3.0, the level of HFC-125 in the distilled HCl is decreased from 51,642 ppm to 40 ppm, or by a factor of 1,290. Obtaining the same purity level of HCl as in this example by conventional distillation is impractical because of the size of column required.

EXAMPLES 3A to 3F

In Examples 3A to 3F, the distillation column has 52 stages, and is operated at a pressure of 265 psia. For the conventional distillation cases the HCl stream to be purified is fed onto column stage 15. For the extractive distillation cases, the HCl stream to be purified is fed onto column stage 35, and the extractant is fed onto column stage 10. The condenser is designated as column stage 1. In each of Examples 3A to 3F, the column distillate rate is adjusted to achieve a quantity of about 0.25 lb/hr of HCl in the column tails stream, i.e., the liquid exiting the bottom of the column. The Tables illustrate the resulting purity of the HCl stream for a particular reflux ratio or flow rate of extractant.

EXAMPLE 3A

In this example, the HCl stream to be purified contains about 5000 lb/hr of HCl, 500 lb/hr of HF and 50 lb/hr of CFC-115 (HCl Mixture #3). The amount of CFC-115 in the overhead purified HCl stream opposite the reflux ratio is tabulated generally in Table X below:

TABLE X

Separation of CFC-115 from HCl Mixture #3 using no Extractant

| Reflux Ratio | Lb/Hr HCl in Distillate | Lb/Hr CFC-115 in Distilled HCl | ppm (wt) of CFC-115 in HCl |
|---|---|---|---|
| 2/1 | 5,000 | 50 | 9,901 |
| 3/1 | 5,000 | 50 | 9,901 |
| 5/1 | 5,000 | 50 | 9,901 |
| 10/1 | 5,000 | 50 | 9,901 |
| 20/1 | 5,000 | 50 | 9,901 |
| 40/1 | 5,000 | 50 | 9,901 |

Table X illustrates that substantially all of the CFC-115 remains mixed with the HCl notwithstanding usage of reflux ratios as high as 40 to 1. Without wishing to be bound by any theory or explanation, it is believed that CFC-115 and HCl are difficult to separate because an azeotrope or near azeotropic mixture is formed, e.g., an azeotrope comprising or consisting essentially of about 4 mole % CFC-115 and 96 mole % HCl. For example, Table X shows that when CFC-115 is fed in at rates less than about the azeotropic concentration with HCl, all the CFC-115 exits with the HCl overhead.

If desired, the previously described process could also be operated under conditions such that the overhead stream consists essentially of the relatively low-boiling CFC-115/HCl azeotrope, and the remaining HCl recovered from the bottom of the column. For example, the system could be operated at approximately 159 psia pressure and −30° C. temperature. The HCl recovered from the bottom of the column in this fashion would be substantially free of CFC-115, e.g., below about 100 ppm CFC-115. However, the total amount of HCl obtained from this column would not be substantially free of CFC-115 because HCl is exiting the overhead distillate with the CFC-115 as an azeotrope. The fraction of total HCl present as the azeotrope would increase with the proportion of CFC-115 in the impure HCl feed. For example, if the feed stream contains about 1100 lb/hr of CFC-115 with about 5000 lb/hr of HCl, then substantially all the HCl would exit the distillation column as an azeotrope such that substantially no HCl, which is free of CFC-115, would be recovered.

EXAMPLE 3B

In this example, the feed stream of impure HCl (Mixture #3) is distilled by conventional means (Example 3A), with the exception that about 10,000 lb/hr of CFC-114a is added at the HCl feed plate along with the HCl (Mixture #4). The CFC-114a is included in the feed in order to compare the efficiency of conventional distillation with and without added CFC-114a, and for later comparison of conventional distillation using CFC-114a added to the feed tray, to extractive distillation using CFC-114a. (In the latter case, Example 3C, the CFC-114a is fed higher in the column than the HCl feed to obtain its full benefit as an extractive distillation agent.) The mount of CFC-115 in the overhead purified HCl stream opposite the reflux ratio using conventional distillation is tabulated in generally in Table XI below:

TABLE XI

Separation of CFC-115 from HCl Mixture #4 using Added CFC-114a at Feed Plate/no Extractant

| Reflux Ratio | Lb/Hr HCl in Distillate | Lb/Hr CFC-115 in Distilled HCl | ppm (wt) of CFC-115 in HCl |
|---|---|---|---|
| 2/1 | 5,000 | 20.7 | 4,123 |
| 3/1 | 5,000 | 22.3 | 4,440 |
| 5/1 | 5,000 | 26.0 | 5,173 |
| 10/1 | 5,000 | 44.6 | 8,841 |
| 20/1 | 5,000 | 49.9 | 9,881 |
| 40/1 | 5,000 | 50.0 | 9,901 |

The addition of CFC-114a at the HCl feed plate has relatively no beneficial effect on HCl purity in comparison to the results which were achieved by Example 3A.

EXAMPLE 3C

In this example, the column is operated at a constant reflux ratio, and varying amounts of CFC-114a are used as the extractive distillation agent. The feed stream of impure HCl is substantially the same as in Example 3A (Mixture #3).

The amount of CFC-115 in the distilled HCl stream at a constant reflux ratio opposite the feed rate of extractant are tabulated generally in Table XII below:

TABLE XII

Separation of CFC-115 from HCl Mixture #3 using CFC-114a as Extractant

| Reflux Ratio | Extractant Rate, Lb/Hr | Lb/Hr CFC-115 in Distilled HCl | ppm (wt) of CFC-115 in HCl |
|---|---|---|---|
| 2/1 | 5,000 | 13.7 | 2,733 |
| 2/1 | 10,000 | 0.03 | 6 |
| 2/1 | 15,000 | <0.001 | <1 |

Table XII illustrates achieving a marked improvement over the results of Example 3B by adding CFC-114a to the distillation column at a feed point located above the HCl feed so that the CFC-114a will function as an extractive agent. Such results indicate that CFC-114a, when fed as an extractant, is effective in increasing the separability of HCl and CFC-115. Table XII also shows that such effectiveness is directly proportional to the feed rate of the CFC-114a.

EXAMPLE 3D

In this example, the feed stream of impure HCl corresponds substantially to that in Example 3B (Mixture #4). Additional CFC-114a is used as extractant. The amount of CFC-115 in the distilled HCl stream at a constant reflux ratio opposite the feed rate of extractant are tabulated generally in Table XIII below:

TABLE XIII

Separation of CFC-115 from HCl Mixture #4 using CFC-114a as Extractant

| Reflux Ratio | Extractant Rate, Lb/Hr | Lb/Hr CFC-115, in Distilled HCl | ppm (wt) of CFC-115 in HCl |
|---|---|---|---|
| 2/1 | 5,000 | 2.7 | 534 |
| 2/1 | 10,000 | 0.01 | 2.2 |
| 2/1 | 15,000 | <0.001 | <1 |

The results illustrated above are comparable to those achieved by Example 3C. However, introducing an additional quantity of CFC-114a into the impure HCl shows an improvement in the purity of the product HCl.

EXAMPLE 3E

In this example, HCFC-124 is used as extractant. All other process conditions are substantially the same as those in Example 3D. The amounts of CFC-115 in the distilled HCl stream at a constant reflux ratio opposite the feed rate of extractant are tabulated generally in Table XIV below:

TABLE XIV

Separation of CFC-115 from HCl Mixture #4 using HCFC-124 as Extractant

| Reflux Ratio | Extractant Rate, Lb/Hr | Lb/Hr CFC-115, in Distilled HCl | ppm (wt) of CFC-115 in HCl |
|---|---|---|---|
| 2/1 | 5,000 | 6.64 | 1,327 |
| 2/1 | 10,000 | 0.23 | 47 |
| 2/1 | 15,000 | 0.01 | 2.5 |
| 2/1 | 20,000 | 0.002 | 0.4 |

EXAMPLE 3F

In this example, HCFC-123 is used as extractant. All other process conditions are substantially the same as Example 3D. The amount of CFC-115 in the distilled HCl stream at a constant reflux ratio opposite the feed rate of extractant are tabulated in Table XV below:

TABLE XV

Separation of CFC-115 from HCl Mixture #4 using HCFC-123 as Extractant

| Reflux Ratio | Extractant Rate, Lb/br | Lb/Hr HCl in Distillate | Lb/Hr CFC-115, in Distilled HCl | ppm (wt) of CFC-115 in HCl |
|---|---|---|---|---|
| 2/1 | 10,000 | 5000 | 6.81 | 1,361 |
| 2/1 | 20,000 | 5000 | 0.38 | 75 |
| 2/1 | 30,000 | 5000 | 0.04 | 8.3 |
| 2/1 | 40,000 | 5000 | 0.01 | 2.0 |
| 2/1 | 50,000 | 5000 | 0.0035 | 0.7 |

Examples 3C to 3F show that CFC-115 may be effectively removed from a mixture comprising HCl and other contaminants by using extractive distillation with fluorocarbons such as CFC-114a, HCFC-124 or HCFC-123. These Examples also show that conventional distillation is incapable of such removal, even when adding CFC-114a to the HCl feed stream.

The following Examples 4 and 5 are provided to illustrate certain aspects of the present invention wherein parts per million (ppm) concentrations are by weight unless otherwise specified. In all of the following Examples, the distillation column has 62 stages, and is operated at a pressure of about 215 psia. The HCl stream to be purified is fed onto column stage 50, and the extractant, if used, is fed onto column stage 20. The condenser is designated as column stage 1. In each of the following examples, the column distillate rate is adjusted to achieve a quantity of about 10 lb/hr of HCl in the column tails stream, i.e., the liquid exiting the bottom of the column. The Tables illustrate the resulting purity of the HCl stream for a particular reflux ratio. The extractive agent, its feed rate, and the composition of the HCl feed stream to be purified can also be varied for tailoring the process to accommodate the purity of product HCl desired.

EXAMPLE 4

In this comparative example, a first feed stream contains 1000 lb/hr HCl and either 1,10 or 100 lb/hr chlorotrifluoromethane (CFC-13). CFC-115 is used as the extractant. The amount of CFC-13 in the distilled HCl stream in parts per million (ppm) by weight opposite the reflux ratio is tabulated in Table XVI below. If desired, the previously described process could also be operated such that the HCl stream to be purified is fed to a column operating under conditions such that the overhead stream consists essentially of the relatively low-boiling CFC-13/HCl azeotrope, and the remaining HCl recovered from the bottom of the column. For example, the system could be operated at approximately 280 psia pressure and with a −20° C. overhead temperature. The HCl recovered from the bottom of this column would be substantially free of CFC-13, e.g., below about 100 ppm CFC-13. However, the total amount of HCl obtained from this column would not be substantially free of CFC-13 because HCl is exiting the overhead distillate with the CFC-13 as an azeotrope. The fraction of total HCl present as the azeotrope would increase with the proportion of CFC-13 in the impure HCl feed.

TABLE XVI

| HCl Feed CFC-13 Concentration (ppm) | Reflux Ratio | Extractant Rate, Lb/Hr | Lb/Hr CFC-13 in distilled HCl | CFC-13 in Distillate HCl (ppm) |
|---|---|---|---|---|
| 1,000 | 10/1 | 25,000 | <0.0001 | <0.1 |
| 1,000 | 10/1 | 10,000 | 0.13 | 131 |
| 10,000 | 10/1 | 25,000 | <0.0001 | <0.1 |
| 100,000 | 3/1 | 25,000 | <0.0001 | <0.1 |

In each of the cases in Table XVI, approximately 150–170 lbs/hr of CFC-115 remains in the distillate HCl. The CFC-115 is removed by the process of Example 3C.

EXAMPLE 5

In this comparative example, a first feed stream contains 1000 lb/hr HCl and either 1 or 10 lb/hr trifluoromethane (HFC-23). HFC-125 is used as the extractant. The amount of HFC-23 in the distilled HCl stream in parts per million (ppm) by weight opposite the reflux ratio is tabulated generally in Table XVII below. If desired, the previously described process could also be operated such that the HCl stream to be purified is fed to a column operating under conditions such that the overhead stream consists essentially of the relatively low-boiling HFC-23/HCl azeotrope, and the remaining HCl recovered from the bottom of the column. For example, the system could be operated at approximately 260 psia pressure and a −20° C. overhead temperature. The HCl recovered form the bottom of this column would be substantially free of HFC-23, e.g., below about 100 ppm HFC-23. However the total amount of HCl obtained from this column would not be substantially free of HFC-23 because HCl is exiting the overhead distillate with the HFC-23 as an azeotrope. The fraction of total HCl present as the azeotrope would increase with the proportion of HFC-23 in the impure HCl feed.

TABLE XVII

| HCl Feed HFC-23 Concentration (ppm) | Reflux Ratio | Extractant Rate, Lb/Hr | Lb/Hr HFC-23 in distilled HCl | HFC-23 in Distillate HCl (ppm) |
|---|---|---|---|---|
| 1,000 | 10/1 | 25,000 | <0.01 | 8.0 |
| 10,000 | 10/1 | 25,000 | 0.08 | 80.0 |

In each of the cases in Table XVII, approximately 24 lb/hr of HFC-125 remains in the distillate HCl. The HFC-125 is removed by using the process of Example 2C.

EXAMPLE 6

This Example demonstrates the existence of azeotropic and azeotrope-like compositions between the binary pair mixtures consisting essentially of HCl and CFC-13, HFC-23 or CFC-115, and HFC-125 and CFC-125.

To determine the relative volatility of each binary pair, the so-called PTx Method was used. In this procedure, for each binary pair, the total absolute pressure in a PTx cell of known volume was measured at a constant temperature for various known binary compositions. These measurements were then reduced to equilibrium vapor and liquid compositions in the cell using the NRTL equation. Samples of selected vapor and liquid sets were obtained and analyzed to verify their respective compositions.

The vapor pressure measured versus the composition in the PTx cell for the HCl/115, HCl/13, HCl/23, and HFC-125/CFC-115 systems are shown in FIGS. 2, 3, 4 and 5 respectively. The experimental data points are shown in each Figure as solid points on each Figure and the curve is drawn by using computer modeling.

Figure 2:
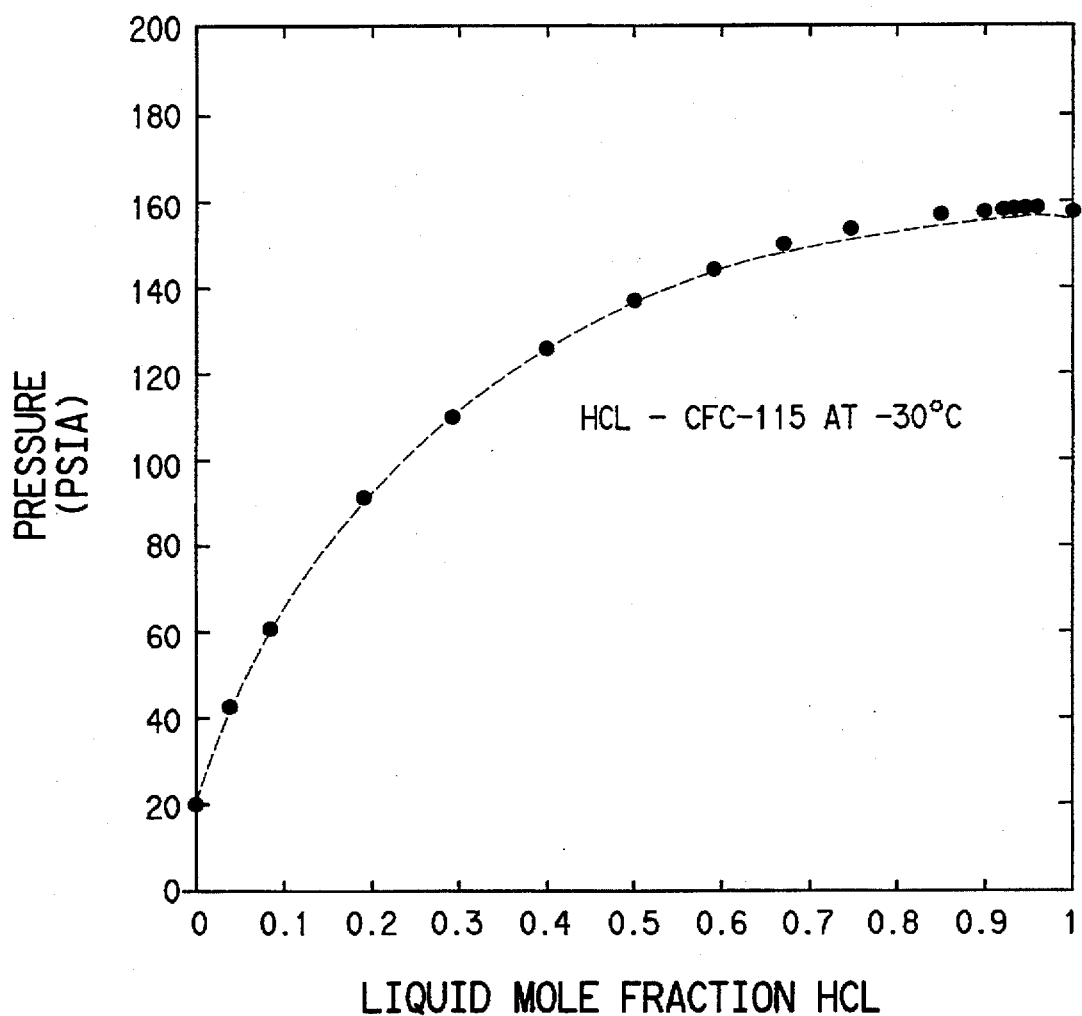
FIG. 2—FIG. 2 is a graphical representation of an azeotropic and azeotrope-like compositions consisting essentially of HCl and CFC-115 at a temperature of about −30° C.

Referring flow to FIG. 2, FIG. 2 illustrates graphically the formation of an azeotropic and azeotrope-like composition consisting essentially of HCl and CFC-115 at −30° C., as indicated by a mixture of about 96.3 mole % HCl and 3.7 mole % CFC-115 having the highest pressure over the range of compositions at this temperature. Based upon these findings, it has been calculated that an azeotropic or azeotrope-like composition of about 95.0 mole % HCl and 5.0 mole % CFC-115 is formed at −50° C. and 75 psia and an azeotropic or azeotrope-like composition of about 99.9 mole % HCl and 0.1 mole % CFC-115 is formed at 25° C. and 690 psia. Accordingly, the present invention provides an azeotropic or azeotrope-like composition consisting essentially of from about 95 to 99.9 mole % HCl and from about 5 to 0.1 mole % CFC-115, said composition having a boiling point of from about −50° C. at 75 psia to about 25° C. at 690 psia.

Figure 3:
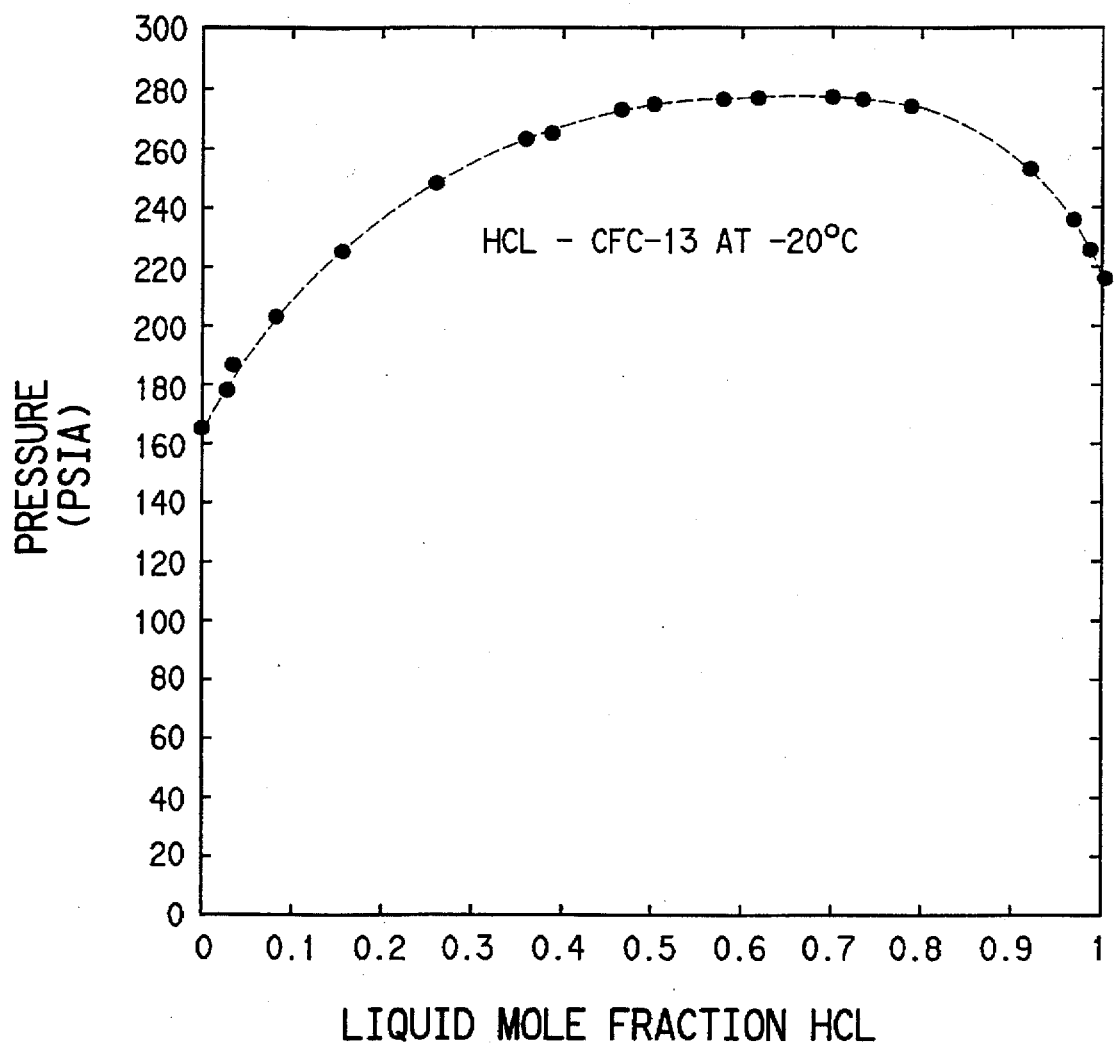
FIG. 3—FIG. 3 is a graphical representation of an azeotropic and azeotrope-like compositions consisting essentially of HCl and CFC-13 at a temperature of about −20° C.

Referring now to FIG. 3, FIG. 3 illustrates graphically the formation of an azeotropic and azeotrope-like composition consisting essentially of HCl and CFC-13 at −20° C., as indicated by a mixture of about 62.4 mole % HCl and 37.6 mole % CFC-13 having the highest pressure over the range of compositions at this temperature. Based upon these findings, it has been calculated that an azeotropic or azeotrope-like composition of about 62.0 mole % HCl and 38.0 mole % CFC-13 is formed at −50° C. and 101 psia; and an azeotropic or azeotrope-like composition of about 61.9 mole % HCl and 38.1 mole % CFC-13 is formed at 25° C. and 866 psia. Accordingly, the present invention provides an azeotropic or azeotrope-like composition consisting essentially of from about 61.9 to 62.4 mole % HCl and from about 38.1 to 37.6 mole % CFC-13, said composition having a boiling point of from about −50° C. at 101 psia to about 25° C. at 866 psia.

Figure 4:
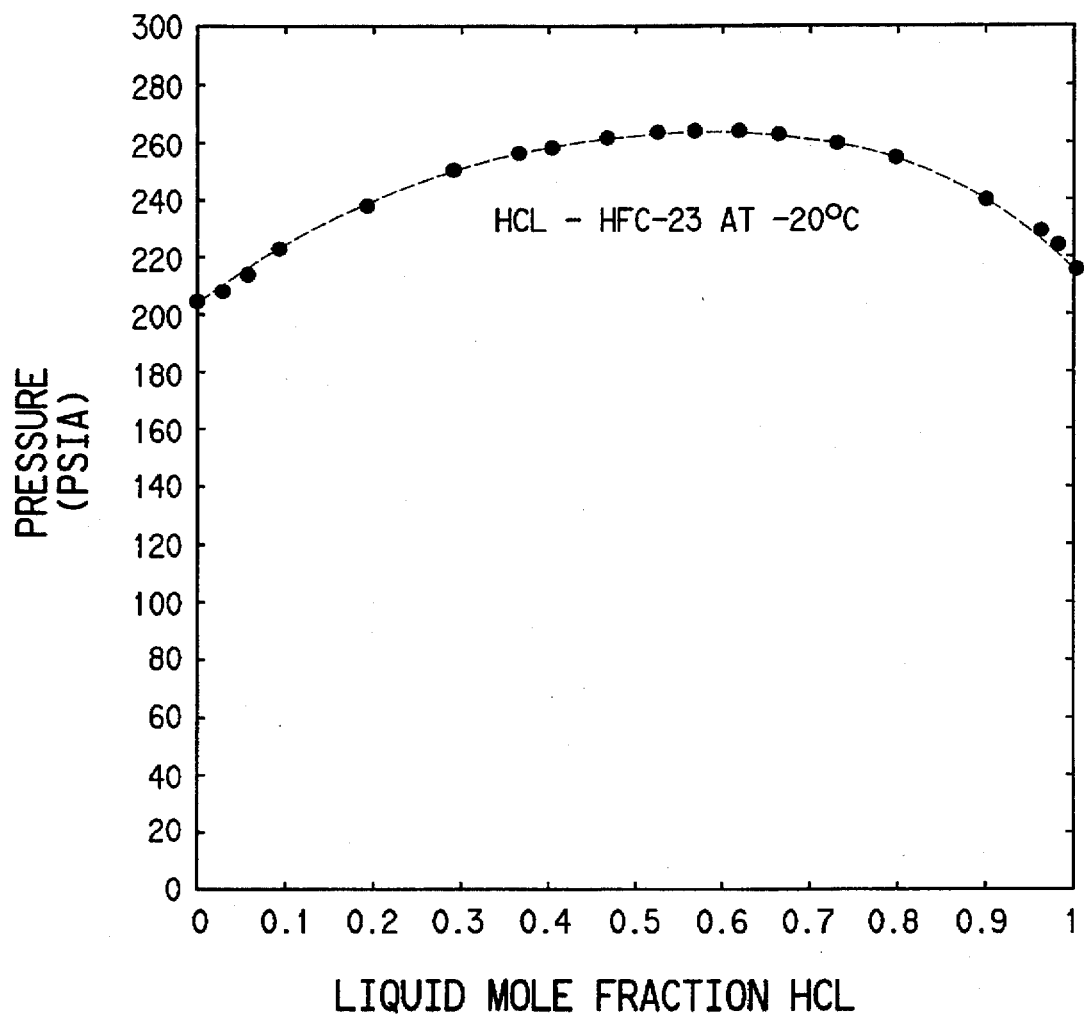
FIG. 4—FIG. 4 is a graphical representation of an azeotropic and azeotrope-like compositions consisting essentially of HCl and HFC-23 at a temperature of about −20° C.

Referring now to FIG. 4, FIG. 4 illustrates graphically the formation of an azeotropic and azeotrope-like composition consisting essentially of HCl and HFC-23 at −20° C., as indicated by a mixture of about 56.9 mole % HCl and 43.1 mole % HFC-23 having the highest pressure over the range of compositions at this temperature. Based upon these findings, it has been calculated that an azeotropic or azeotrope-like composition of about 59.2 mole % HCl and 40.8 mole % HFC-23 is formed at −50° C. and 92.7 psia and an azeotropic or azeotrope-like composition of about 49.2 mole % HCl and 50.8 mole % HFC-23 is formed at 25° C. and 866 psia. Accordingly, the present invention provides an azeotropic or azeotrope-like composition consisting essentially of from about 59.2 to 49.2 mole % HCl and from about 40.8 to 50.8 mole % HFC-23, said composition having a boiling point of from about −50° C. at 93 psia to about 25° C. at 897 psia.

Figure 5:
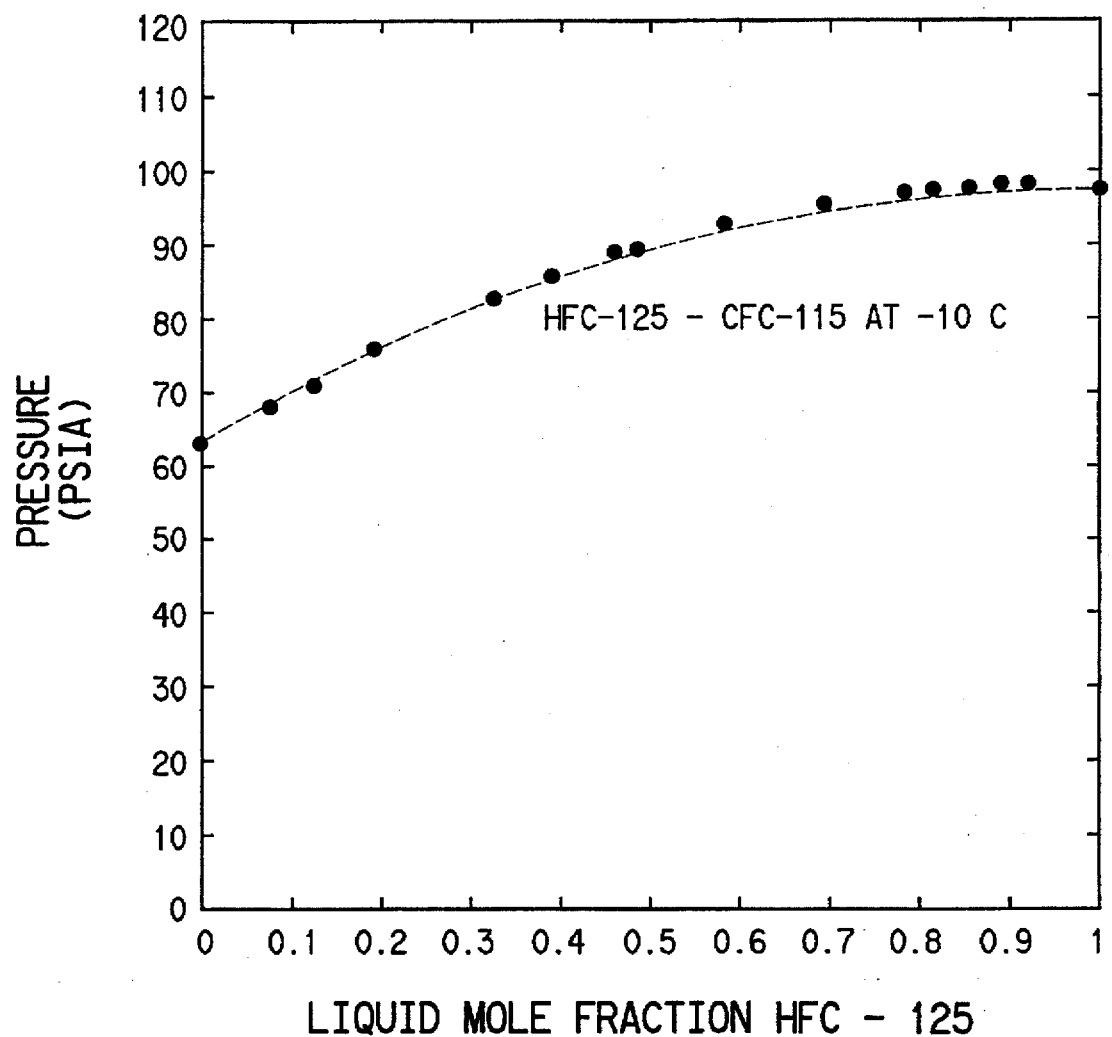
FIG. 5—FIG. 5 is a graphical representation of the vapor pressure measurements in a PTx cell for a HFC-125/CFC-115 system as a function of composition at a temperature of about −10° C.
Figure 6:
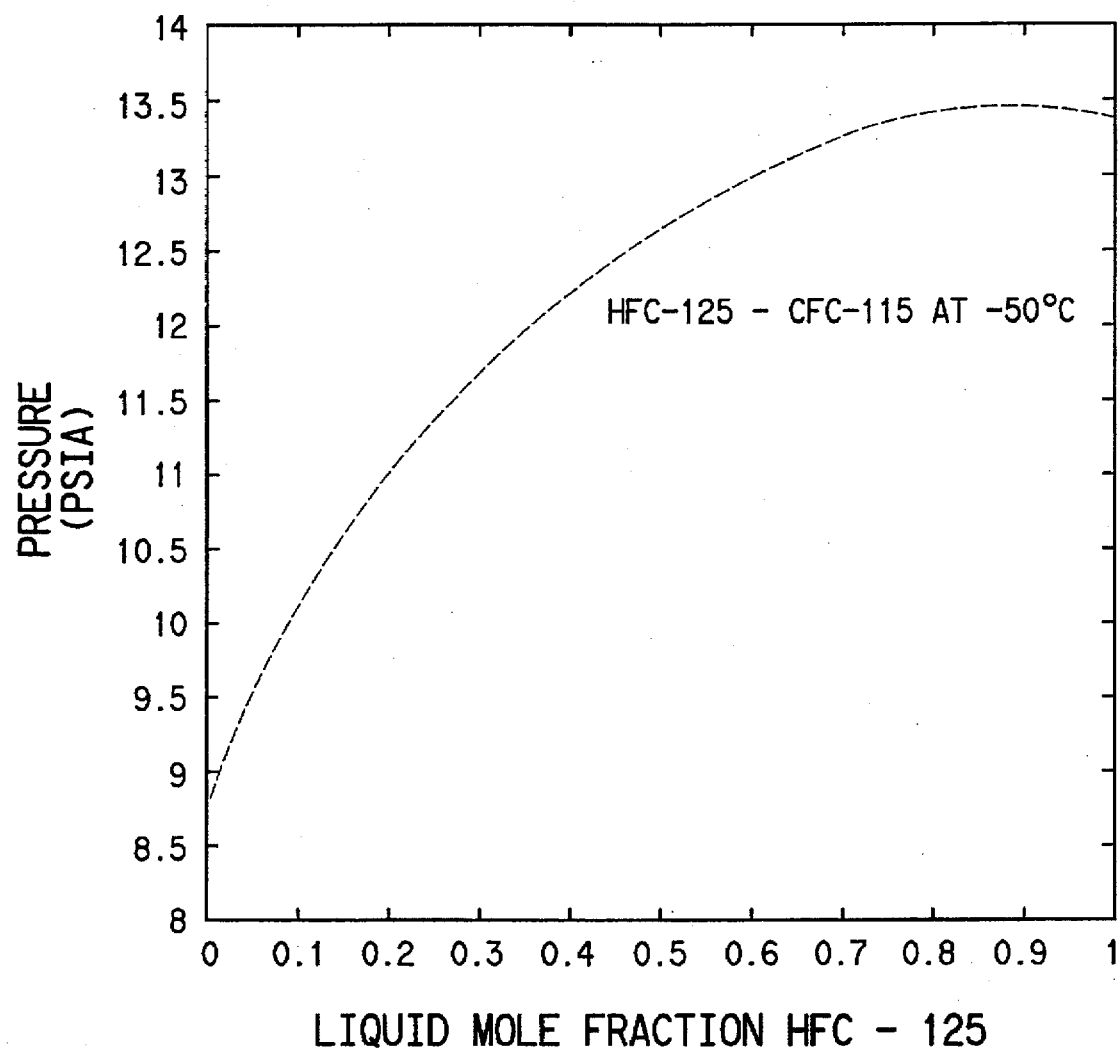
FIG. 6—FIG. 6 is a graphical representation of an azeotropic and azeotrope-like compositions consisting essentially of HFC-125 and CFC-115 at a temperature of about −50° C.

Referring now to FIG. 5, FIG. 5 illustrates graphically the results of the PTx measurements obtained from the HFC-125 and CFC-115 combinations at −10° C. Based upon these findings, it has been calculated that an azeotropic or azeotrope-like composition of about 87.0 mole % HFC-125 and 13.0 mole % CFC-115 is formed at −60° C. and 8.0 psia and an azeotropic or azeotrope-like composition of about 99.3 mole % HFC-125 and 0.7 mole % CFC-115 is formed at −5° C. and 83. psia. The results of these calculations for −50° C. are shown in FIG. 6. FIG. 6 illustrates graphically the formation of an azeotropic and azeotrope-like composition consisting essentially of 89.3 mole % HFC-125 and 10.7 mole % CFC-115, as indicated by that combination having the highest pressure over the range of compositions at this temperature. Accordingly, the present invention provides an azeotropic or azeotrope-like composition consisting essentially of from about 87.0 to 99.3 mole % HFC-125 and from about 13.0 to 0.7 mole % CFC-115, said composition having a boiling point of from about −60° C. at 8.0 psia to about −5° C. at about 83.0 psia.

While certain aspects of the invention have been described above in detail, a person having ordinary skill in this art would recognize that other embodiments and variations are encompassed by the appended claims.

The following is claimed:

1. An azeotropic or azeotrope-like composition consisting essentially of about 0.1 to 5 mole % chloropentafluoroethane and about 95 to 99.9 mole % HCl wherein said composition has a boiling point that ranges from about −50° C. at about 75 psia to about 25° C. at about 690 psia.

2. The composition of claim 1 wherein the relative volatility is 1.0.

3. The composition of claims or 2 wherein the vapor pressure of the composition is greater than HCl or chloropentafluoroethane.

* * * * *